United States Patent [19]
Jerome

[11] Patent Number: 6,125,476
[45] Date of Patent: Oct. 3, 2000

[54] MALE UNDERGARMENT

[76] Inventor: Sandra A. Jerome, 12 Gowing Rd., Hudson, N.H. 03051

[21] Appl. No.: 09/226,263

[22] Filed: Jan. 7, 1999

[51] Int. Cl.[7] .................................................... A41B 9/00
[52] U.S. Cl. ................................................. 2/403; 2/400
[58] Field of Search ..................... 2/400–408; 604/385.1, 604/385.2, 358, 366–396

[56] References Cited

U.S. PATENT DOCUMENTS

| | | | |
|---|---|---|---|
| 4,762,521 | 8/1988 | Roessler et al. | 604/385.1 |
| 5,308,344 | 5/1994 | Toth | 604/378 |
| 5,645,543 | 7/1997 | Nomura et al. | 604/396 |
| 5,849,002 | 12/1998 | Carlos et al. | 604/368 |
| 5,873,870 | 2/1999 | Seitz et al. | 604/385.1 |
| 5,885,267 | 3/1999 | Mishima et al. | 604/378 |
| 5,906,602 | 5/1999 | Weber et al. | 604/385.1 |
| 5,957,907 | 9/1999 | Sauer | 604/385.1 |

*Primary Examiner*—Gloria M. Hale

[57] ABSTRACT

A male undergarment for wear by a bowel incontinent user. The male undergarment includes an undergarment having front portion, a back portion, a bottom crotch portion, an upper waist opening, and a pair of lower leg openings. The undergarment has substantially inner and outer layers. The undergarment has a pair of generally parallel opposite longitudinal side slits therethrough separating upper regions of the front and back portions from one another. The back portion of the undergarment has a pair of attachment straps coupled thereto which are detachably attached to the front portion of the undergarment. A generally hourglass-shaped flexible shield is interposed between the inner and outer layers of the undergarment and positioned in the bottom crotch portion of the undergarment. The shield comprises a water-impermeable material to prevent the passage of water therethrough.

19 Claims, 2 Drawing Sheets

MALE UNDERGARMENT

BACKGROUND OF THE INVENTION

1. Field of the Invention

The present invention relates to male undergarments and more particularly pertains to a new male undergarment for wear by a bowel incontinent user.

2. Description of the Prior Art

The use of male undergarments is known in the prior art. More specifically, male undergarments heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,009,649; U.S. Pat. No. 5,207,663; U.S. Pat. No. Des. 309,020; U.S. Pat. No. 5,098,419; U.S. Pat. No. 4,821,342; and U.S. Pat. No. 4,758,241.

While these devices fulfill their respective, particular objectives and requirements, the aforementioned patents do not disclose a new male undergarment. The inventive device includes an undergarment having front portion, a back portion, a bottom crotch portion, an upper waist opening, and a pair of lower leg openings. The undergarment has substantially inner and outer layers. The undergarment has a pair of generally parallel opposite longitudinal side slits therethrough separating upper regions of the front and back portions from one another. The back portion of the undergarment has a pair of attachment straps coupled thereto which are detachably attached to the front portion of the undergarment. A generally hourglass-shaped flexible shield is interposed between the inner and outer layers of the undergarment and positioned in the bottom crotch portion of the undergarment. The shield comprises a water-impermeable material to prevent the passage of water therethrough.

In these respects, the male undergarment according to the present invention substantially departs from the conventional concepts and designs of the prior art, and in so doing provides an apparatus primarily developed for the purpose of wear by a bowel incontinent user.

SUMMARY OF THE INVENTION

In view of the foregoing disadvantages inherent in the known types of male undergarments now present in the prior art, the present invention provides a new male undergarment construction wherein the same can be utilized for wear by a bowel incontinent user.

The general purpose of the present invention, which will be described subsequently in greater detail, is to provide a new male undergarment apparatus and method which has many of the advantages of the male undergarments mentioned heretofore and many novel features that result in a new male undergarment which is not anticipated, rendered obvious, suggested, or even implied by any of the prior art male undergarments, either alone or in any combination thereof.

To attain this, the present invention generally comprises an undergarment having front portion, a back portion, a bottom crotch portion, an upper waist opening, and a pair of lower leg openings. The undergarment has substantially inner and outer layers. The undergarment has a pair of generally parallel opposite longitudinal side slits therethrough separating upper regions of the front and back portions from one another. The back portion of the undergarment has a pair of attachment straps coupled thereto which are detachably attached to the front portion of the undergarment. A generally hourglass-shaped flexible shield is interposed between the inner and outer layers of the undergarment and positioned in the bottom crotch portion of the undergarment. The shield comprises a water-impermeable material to prevent the passage of water therethrough.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new male undergarment apparatus and method which has many of the advantages of the male undergarments mentioned heretofore and many novel features that result in a new male undergarment which is not anticipated, rendered obvious, suggested, or even implied by any of the prior art male undergarments, either alone or in any combination thereof.

It is another object of the present invention to provide a new male undergarment which may be easily and efficiently manufactured and marketed.

It is a further object of the present invention to provide a new male undergarment which is of a durable and reliable construction.

An even further object of the present invention is to provide a new male undergarment which is susceptible of a low cost of manufacture with regard to both materials and labor, and which accordingly is then susceptible of low prices of sale to the consuming public, thereby making such male undergarment economically available to the buying public.

Still yet another object of the present invention is to provide a new male undergarment which provides in the apparatuses and methods of the prior art some of the advantages thereof, while simultaneously overcoming some of the disadvantages normally associated therewith.

Still another object of the present invention is to provide a new male undergarment for wear by a bowel incontinent user.

Yet another object of the present invention is to provide a new male undergarment which includes an undergarment having front portion, a back portion, a bottom crotch portion, an upper waist opening, and a pair of lower leg openings. The undergarment has substantially inner and outer layers. The undergarment has a pair of generally parallel opposite longitudinal side slits therethrough separating upper regions of the front and back portions from one another. The back portion of the undergarment has a pair of attachment straps coupled thereto which are detachably attached to the front portion of the undergarment. A generally hourglass-shaped flexible shield is interposed between the inner and outer layers of the undergarment and positioned in the bottom crotch portion of the undergarment. The shield comprises a water-impermeable material to prevent the passage of water therethrough.

Still yet another object of the present invention is to provide a new male undergarment that protects a user from becoming wet and soiled from incontinence.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
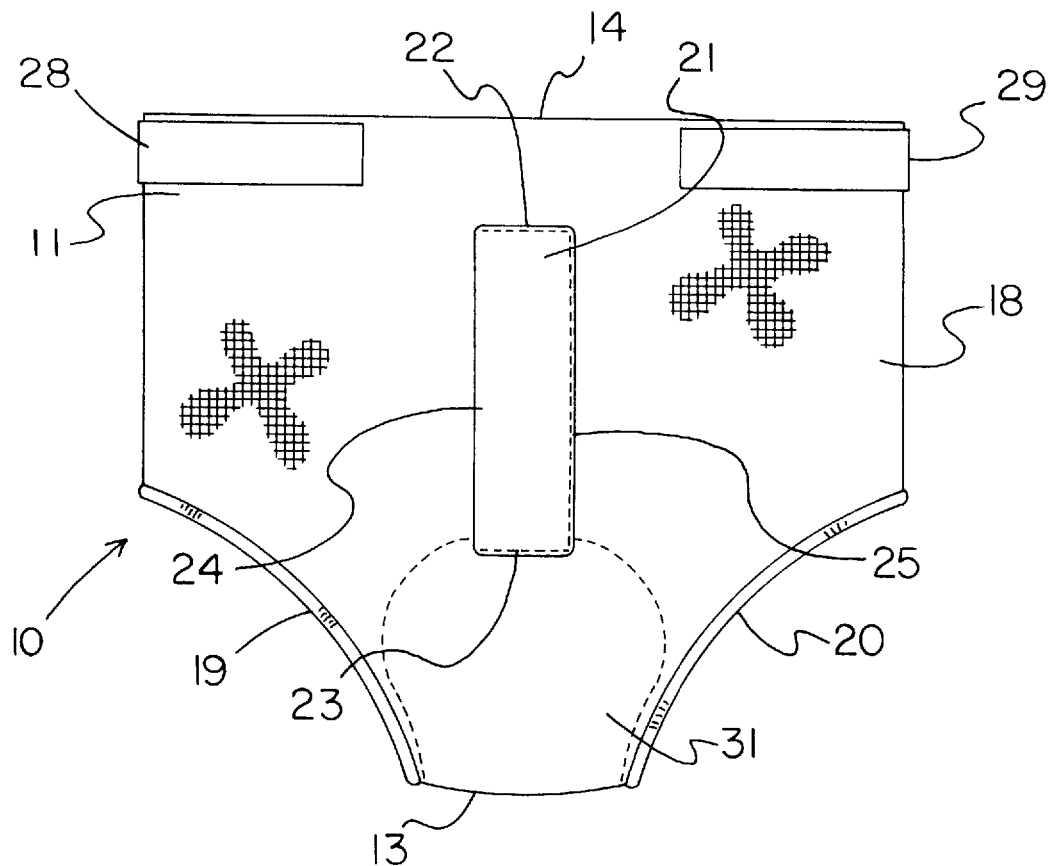
FIG. 1 is a schematic front view of a new male undergarment according to the present invention.

With reference now to the drawings, and in particular to FIGS. 1 through 4 thereof, a new male undergarment embodying the principles and concepts of the present invention will be described.

As best illustrated in FIGS. 1 through 4, the male undergarment generally comprises an undergarment having front portion, a back portion, a bottom crotch portion, an upper waist opening, and a pair of lower leg openings. The undergarment has substantially inner and outer layers. The undergarment has a pair of generally parallel opposite longitudinal side slits therethrough separating upper regions of the front and back portions from one another. The back portion of the undergarment has a pair of attachment straps coupled thereto which are detachably attached to the front portion of the undergarment. A generally hourglass-shaped flexible shield is interposed between the inner and outer layers of the undergarment and positioned in the bottom crotch portion of the undergarment. The shield comprises a water-impermeable material to prevent the passage of water therethrough.

In closer detail, the undergarment 10 has front portion 11, a back portion 12, a bottom crotch portion 13, an upper waist opening 14, and a pair of lower leg openings 15,16. The undergarment has substantially inner and outer layers. The inner and outer layers preferably comprise a cotton fabric material for providing optimal comfort and absorbency of moisture. Each of the lower leg openings of the undergarment has an elastic band 19,20 along the outer periphery of the respective lower leg opening to constrict the lower leg opening around the legs of the wear extending through the lower leg openings.

The front portion of the undergarment has a hole therethrough and a generally rectangular cover flap 21 covering the hole. The hole is designed for extending the penis of the wearer therethrough. The cover flap has a generally rectangular outer perimeter has a pair of ends 22,23 and a pair of sides 24,25. The ends and one of the sides of the cover flap are coupled to the outer layer of the undergarment. An upper end 22 of the pair of ends of the cover flap is positioned towards the upper waist opening of the undergarment and a lower end 23 of the pair of ends of the cover flap is positioned towards the bottom crotch portion of the undergarment.

Figure 4:
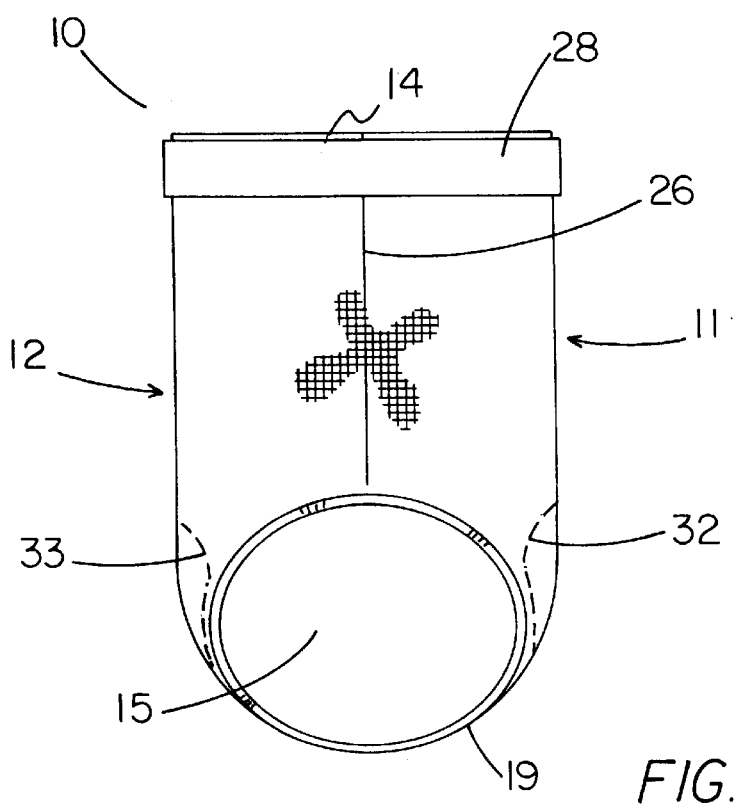
FIG. 4 is a schematic side view of the present invention.

The undergarment has a pair of generally parallel opposite longitudinal side slits 26,27 therethrough. One of the longitudinal side slits extends from the upper waist opening towards one of the lower leg openings and the other longitudinal side slit extends from the upper waist opening towards the other lower leg opening. The longitudinal side slits separate upper regions of the front and back portions from one another. As best illustrated in FIG. 4, each of the longitudinal side slits is spaced apart from the outer periphery of the associated lower leg opening to define a corresponding connecting region connecting the front and back portions of the undergarment together between the respective longitudinal side slit and the associated lower leg opening. The longitudinal side slits each has have a length several times greater than a span of the associated connecting region defined between the respective longitudinal side slit and the associated outer periphery of the associated lower leg opening.

Figure 3:
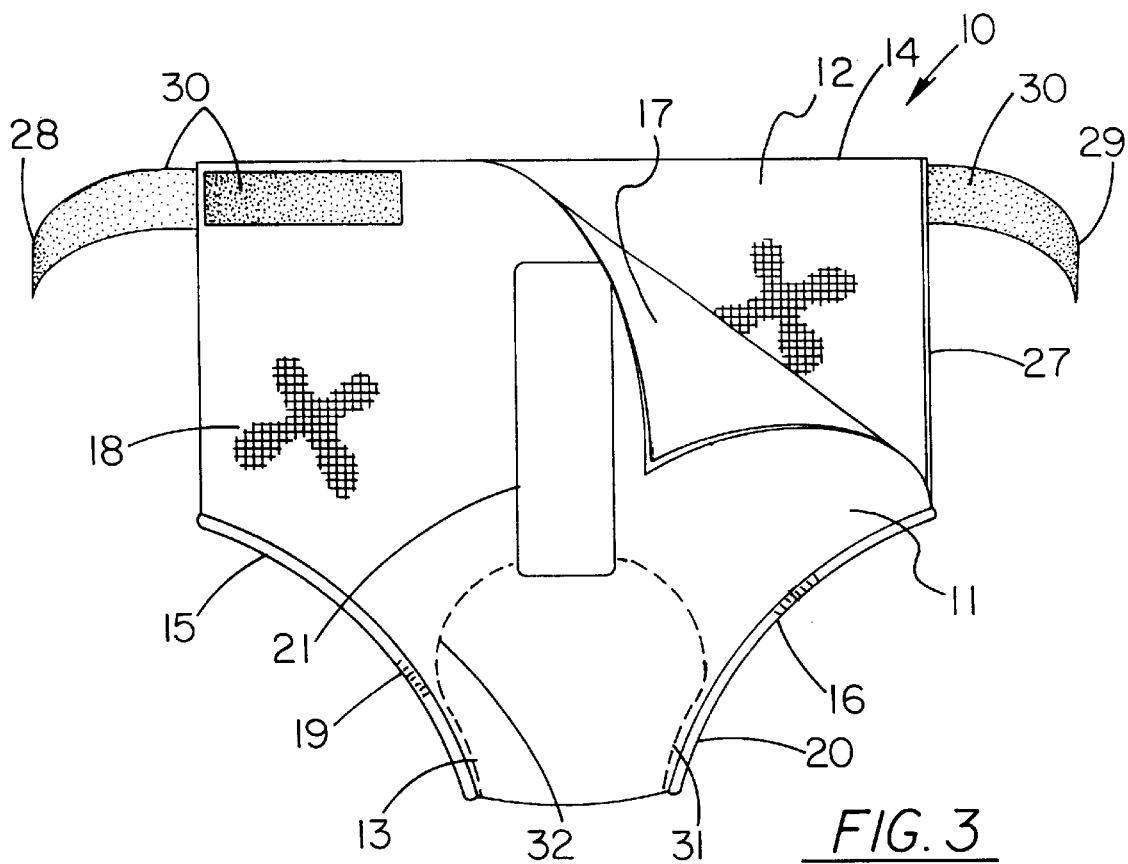
FIG. 3 is another schematic front view of the present invention.

The back portion of the undergarment has a pair of attachment straps 28,29 coupled thereto. The attachment straps are positioned adjacent the upper waist opening of the undergarment. One of the attachment straps is positioned adjacent one of the longitudinal side slits. The other of the attachment straps is positioned adjacent the other of the longitudinal side slits. The attachment straps are detachably attached to the front portion of the undergarment to couple the upper regions of the front and back portions together around the lower torso of the wearer. In use, the attachment straps are designed for securing the undergarment around the waist of the wearer. Ideally, hooks and loops fasteners 30 detachably attach the attachment straps to the front portion of the undergarment as illustrated in FIG. 3.

Figure 2:
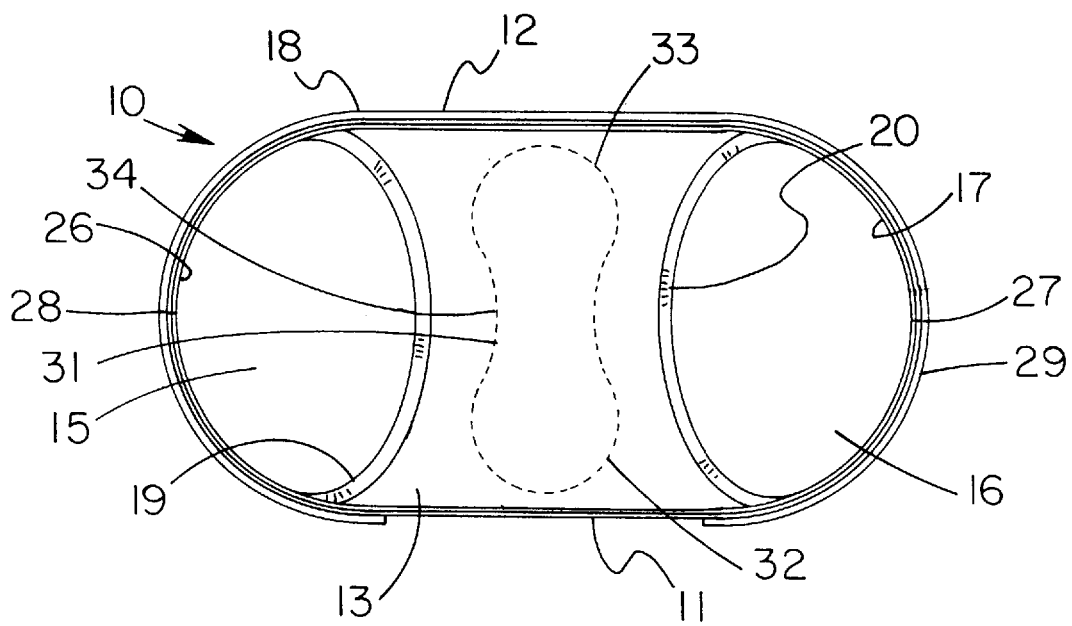
FIG. 2 is a schematic top view of the present invention.

As with reference to FIGS. 1 and 2, a generally hourglass-shaped flexible shield 31 is interposed between the inner and outer layers of the undergarment and positioned in the bottom crotch portion of the undergarment. The shield comprises a water-impermeable material to prevent the passage of water and water based liquids therethrough.

Ideally, the shield comprises a flexible plastic material. The shield has front and back lobes 32,33 and a middle constriction 34 interposed between the front and back lobes of the shield. The front lobe 32 of the shield is extended into the front portion of the undergarment and the back lobe 32 of the shield is extended into the back portion of the undergarment. As illustrated in FIG. 1, a portion of the front lobe is extended between the upper and lower ends of the cover flap with this portion of the front lobe positioned adjacent the lower end of the cover flap.

The shield has a longitudinal axis extending between the front and back lobes. The cover flap has a longitudinal axis extending between the ends of the cover flap. Preferably, the longitudinal axes of the shield and the cover flap lie in substantially parallel planes to one another. The front and back lobes of the shield each have a maximum width defined perpendicular to the longitudinal axis of the shield about equal to one another. The middle constriction of the shield has a minimum width defined perpendicular to the longitudinal axis of the shield less than three-quarters of the maximum width of the front lobe and less than about three-quarters the maximum width of the back lobe for maximum comfort of the shield between the legs of the wearer.

In use, the undergarment is worn on the lower torso of user to protect the user from wetness and soiling from bowel incontinence. To remove the undergarment, the user detaches the attachment straps from the front portion so that the user may separate the upper regions of the front and back portions and slip out of the undergarment.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An incontinence undergarment system for a male user, comprising:

an undergarment having front portion, a back portion, a bottom crotch portion, an upper waist opening, and a pair of lower leg openings;

said undergarment having substantially inner and outer layers;

said undergarment having a pair of generally parallel opposite longitudinal side slits therethrough, one of said longitudinal side slits extending from said upper waist opening towards one of said lower leg openings, the other of said longitudinal side slit extending from said upper waist opening towards the other of said lower leg openings;

said longitudinal side slits separating upper regions of said front and back portions from one another;

said back portion of said undergarment having a pair of attachment straps coupled thereto, said attachment straps being positioned adjacent said upper waist opening of said undergarment;

said attachment straps being detachably attached to said front portion of said undergarment to couple said upper regions of said front and back portions together;

a generally hourglass-shaped flexible shield being interposed between said inner and outer layers of said undergarment, said shield being positioned in said bottom crotch portion of said undergarment;

said shield comprising a water-impermeable material to prevent the passage of water therethrough; and wherein said front portion of said undergarment having a hole therethrough and a generally rectangular cover flap covering said hole, said cover flap having a generally rectangular outer perimeter having a pair of ends and a pair of sides, said ends and one of said sides of said cover flap being coupled to said outer layer of said undergarment.

2. The incontinence undergarment system of claim 1, wherein said lower leg openings of said undergarment each have an outer periphery, each of said lower leg openings of said undergarment having an elastic band along said outer periphery of the respective lower leg opening.

3. The incontinence undergarment of claim 1, wherein an upper end of said pair of ends of said cover flap is positioned towards said upper waist opening of said undergarment, and a lower end of said pair of ends of said cover flap is positioned towards said bottom crotch portion of said undergarment.

4. The incontinence undergarment system of claim 3, wherein said shield has front and back lobes and a middle constriction interposed between said front and back lobes of said shield, said front lobe of said shield being extended into said front portion of said undergarment, said back lobe of said shield being extended into said back portion of said undergarment, and wherein a portion of said front lobe is extended between said upper and lower ends of said cover flap.

5. The incontinence undergarment system of claim 4, wherein said shield has a longitudinal axis extending between said front and back lobes, wherein said cover flap has a longitudinal axis extending between said ends of said cover flap, and wherein said longitudinal axes of said shield and said cover flap lie in substantially parallel planes to one another.

6. The incontinence undergarment system of claim 4, wherein said front and back lobes of said shield each have a maximum width defined perpendicular to said longitudinal axis of said shield about equal to one another, wherein said middle constriction of said shield has a minimum width defined perpendicular to said longitudinal axis of said shield less than three-quarters of said maximum width of said front lobe and less than about three-quarters said maximum width of said back lobe.

7. The incontinence undergarment system of claim 1, wherein each of said longitudinal side slits is spaced apart from said outer periphery of the associated lower leg opening to define a corresponding connecting region connecting said front and back portions of said undergarment together between the respective longitudinal side slit and the associated lower leg opening.

8. The incontinence undergarment system of claim 7, wherein said longitudinal side slits each have a length several times greater than a span of the associated connecting region defined between the respective longitudinal side slit and the associated outer periphery of the associated lower leg opening.

9. The incontinence undergarment system of claim 1, wherein hooks and loops fasteners detachably attach said attachment straps to the front portion of said undergarment.

10. An incontinence undergarment system, comprising:

an undergarment having front portion, a back portion, a bottom crotch portion, an upper waist opening, and a pair of lower leg openings;

said undergarment having substantially inner and outer layers, said inner and outer layers comprising a cotton fabric material;

lower leg openings of said undergarment each having an outer periphery, each of said lower leg openings of said undergarment having an elastic band along said outer periphery of the respective lower leg opening;

said front portion of said undergarment having a hole therethrough and a generally rectangular cover flap covering said hole;

said cover flap having a generally rectangular outer perimeter having a pair of ends and a pair of sides, said ends and one of said sides of said cover flap being coupled to said outer layer of said undergarment;

an upper end of said pair of ends of said cover flap being positioned towards said upper waist opening of said undergarment, a lower end of said pair of ends of said cover flap being positioned towards said bottom crotch portion of said undergarment;

said undergarment having a pair of generally parallel opposite longitudinal side slits therethrough, one of said longitudinal side slits extending from said upper waist opening towards one of said lower leg openings, the other of said longitudinal side slit extending from said upper waist opening towards the other of said lower leg openings;

said longitudinal side slits separating upper regions of said front and back portions from one another;

each of said longitudinal side slits being spaced apart from said outer periphery of the associated lower leg opening to define a corresponding connecting region connecting said front and back portions of said undergarment together between the respective longitudinal side slit and the associated lower leg opening;

said longitudinal side slits each having a length several times greater than a span of the associated connecting region defined between the respective longitudinal side slit and the associated outer periphery of the associated lower leg opening;

said back portion of said undergarment having a pair of attachment straps coupled thereto, said attachment straps being positioned adjacent said upper waist opening of said undergarment;

one of said attachment straps being positioned adjacent one of said longitudinal side slits, the other of said attachment straps being positioned adjacent the other of said longitudinal side slits;

said attachment straps being detachably attached to said front portion of said undergarment to couple said upper regions of said front and back portions together;

wherein hooks and loops fasteners detachably attach said attachment straps to the front portion of said undergarment;

a generally hourglass-shaped flexible shield being interposed between said inner and outer layers of said undergarment, said shield being positioned in said bottom crotch portion of said undergarment;

said shield comprising a water-impermeable material to prevent the passage of water therethrough;

said shield comprising a flexible plastic material;

said shield having front and back lobes and a middle constriction interposed between said front and back lobes of said shield;

said front lobe of said shield being extended into said front portion of said undergarment, said back lobe of said shield being extended into said back portion of said undergarment;

a portion of said front lobe being extended between said upper and lower ends of said cover flap, said portion of said front lobe being positioned adjacent said lower end of said cover flap;

said shield having a longitudinal axis extending between said front and back lobes, said cover flap having a longitudinal axis extending between said ends of said cover flap, said longitudinal axes of said shield and said cover flap lying in substantially parallel planes to one another;

said front and back lobes of said shield each having a maximum width defined perpendicular to said longitudinal axis of said shield about equal to one another; and said middle constriction of said shield having a minimum width defined perpendicular to said longitudinal axis of said shield less than three-quarters of said maximum width of said front lobe and less than about three-quarters said maximum width of said back lobe.

11. An incontinence undergarment system for a male user, comprising:

an undergarment having front portion, a back portion, a bottom crotch portion, an upper waist opening, and a pair of lower leg openings;

said undergarment having substantially inner and outer layers;

said undergarment having a pair of generally parallel opposite longitudinal side slits therethrough, one of said longitudinal side slits extending from said upper waist opening towards one of said lower leg openings, the other of said longitudinal side slit extending from said upper waist opening towards the other of said lower leg openings;

said longitudinal side slits separating upper regions of said front and back portions from one another;

said back portion of said undergarment having a pair of attachment straps coupled thereto, said attachment straps being positioned adjacent said upper waist opening of said undergarment;

said attachment straps being detachably attached to said front portion of said undergarment to couple said upper regions of said front and back portions together;

a generally hourglass-shaped flexible shield being interposed between said inner and outer layers of said undergarment, said shield being positioned in said bottom crotch portion of said undergarment;

said shield comprising a water-impermeable material to prevent the passage of water therethrough; and wherein said front portion of said undergarment having a hole therethrough and a cover flap covering said hole, said cover flap having an outer perimeter having a pair of ends and a pair of sides, said ends and one of said sides of said cover flap being coupled to said outer layer of said undergarment.

12. The incontinence undergarment system of claim 11, wherein the outer perimeter of said cover flap is generally rectangular.

13. The incontinence undergarment of claim 11, wherein an upper end of said pair of ends of said cover flap is positioned towards said upper waist opening of said undergarment, and a lower end of said pair of ends of said cover flap is positioned towards said bottom crotch portion of said undergarment.

14. The incontinence undergarment system of claim 11, wherein said shield has front and back lobes and a middle constriction interposed between said front and back lobes of said shield, said front lobe of said shield being extended into said front portion of said undergarment, said back lobe of said shield being extended into said back portion of said undergarment, and wherein a portion of said front lobe is extended between said upper and lower ends of said cover flap.

15. The incontinence undergarment system of claim 11, wherein said shield has a longitudinal axis extending between said front and back lobes, wherein said cover flap has a longitudinal axis extending between said ends of said cover flap, and wherein said longitudinal axes of said shield and said cover flap lie in substantially parallel planes to one another.

16. The incontinence undergarment system of claim 11, wherein said front and back lobes of said shield each have a maximum width defined perpendicular to said longitudinal axis of said shield about equal to one another, wherein said middle constriction of said shield has a minimum width defined perpendicular to said longitudinal axis of said shield less than three-quarters of said maximum width of said front lobe and less than about three-quarters said maximum width of said back lobe.

17. The incontinence undergarment system of claim 11, wherein each of said longitudinal side slits is spaced apart from said outer periphery of the associated lower leg opening to define a corresponding connecting region connecting said front and back portions of said undergarment together between the respective longitudinal side slit and the associated lower leg opening.

18. The incontinence undergarment system of claim 17, wherein said longitudinal side slits each have a length several times greater than a span of the associated connecting region defined between the respective longitudinal side slit and the associated outer periphery of the associated lower leg opening.

19. The incontinence undergarment system of claim 11, wherein hooks and loops fasteners detachably attach said attachment straps to the front portion of said undergarment.

* * * * *